United States Patent [19]

Haefele

[11] 4,025,616

[45] * May 24, 1977

[54] ORAL COMPOSITIONS FOR PLAQUE, CARIES AND CALCULUS RETARDATION WITH REDUCED STAINING TENDENCIES

[75] Inventor: John William Haefele, Sarasota, Fla.

[73] Assignee: The Procter & Gamble Company, Cincinnati, Ohio

[ * ] Notice: The portion of the term of this patent subsequent to Jan. 20, 1993, has been disclaimed.

[22] Filed: Nov. 25, 1975

[21] Appl. No.: 635,030

Related U.S. Application Data

[63] Continuation of Ser. No. 338,464, March 6, 1973, abandoned, which is a continuation-in-part of Ser. No. 267,816, June 30, 1972, abandoned.

[52] U.S. Cl. .................................... 424/52; 424/54
[51] Int. Cl.² ..................... A61K 7/18; A61K 7/22
[58] Field of Search .............................. 424/48–58

[56] References Cited

UNITED STATES PATENTS

| 3,488,419 | 1/1970 | McCune et al. | 424/49 |
| 3,934,002 | 1/1976 | Haefele | 424/54 |
| 3,937,805 | 2/1976 | Harrison | 424/52 |
| 3,937,807 | 2/1976 | Haefele | 424/52 |

*Primary Examiner*—Shep K. Rose
*Attorney, Agent, or Firm*—Ronald L. Hemingway; Robert B. Aylor; George W. Allen

[57] ABSTRACT

Oral compositions such as toothpastes, mouthwashes and the like containing an insoluble bis-biguanide compound which inhibits the formation of plaque and caries with reduced tendency of the bis-biguanide compound to produce a stain on oral surfaces as compared to soluble compounds.

21 Claims, No Drawings

ORAL COMPOSITIONS FOR PLAQUE, CARIES AND CALCULUS RETARDATION WITH REDUCED STAINING TENDENCIES

CROSS REFERENCE TO RELATED APPLICATIONS

This application is a continuation of my abandoned application having Ser. No. 338,464, filed Mar. 6, 1973 which is in turn a continuation-in-part of my abandoned application Ser. No. 267,816, filed June 30, 1972.

BACKGROUND OF THE INVENTION

The field of this invention is "oral compositions" which term is used herein to designate products which in the ordinary course of usage are retained in the oral cavity for a time and in a manner sufficient to contact essentially all of the dental surfaces, but are not intentionally ingested. Such products include, for example, dentifrices, mouthwashes, prophylaxis pastes and topical solutions.

The bis-biguanide cations of this invention are known, having been disclosed in U.S. Pat. No. 2,684,924, Rose et al., patented July 27, 1954; U.S. Pat. No. 2,990,425, Senior et al., patented June 27, 1961; U.S. Pat. No. 2,830,006, Burtwell et al., patented Apr. 8, 1958; and U.S. Pat. No. 2,863,019, Burtwell et al., patented Dec. 9, 1958. Similarly, the phosphorus-containing anti-calculus agents are known, having been disclosed in U.S. Pat. No. 3,488,419, H. W. McCune and N. B. Tucker, patented Jan. 6, 1970; U.S. Pat. No. 3,553,314, M. D. Francis, patented Jan. 5, 1971; U.S. Pat. No. 3,553,315, M. D. Francis, patented Jan. 5, 1971; U.S. Pat. No. 3,535,420, H. W. McCune and N. B. Tucker, patented Oct. 20, 1970; U.S. Pat. No. 3,535,421, W. W. Briner and J. S. Widder, patented Oct. 20, 1970; U.S. Pat. No. 3,560,608, W. J. Griebstein, R. J. Grabenstetter and J. S. Widder, patented Feb. 2, 1971; U.S. Pat. No. 3,584,116, M. D. Francis, patented June 8, 1971; U.S. Pat. No. 3,639,569, R. F. Medcalf, patented Feb. 1, 1972; etc. All of said patents are incorporated herein by reference. The anti-plaque activity of the soluble bis-biguanides is known.

SUMMARY OF THE INVENTION

It has now been discovered that if the water-insoluble bis-biguanide compounds disclosed herein are used in oral compositions, the stain that is normally caused by continuous use of the water-soluble bis-biguanide compounds is effectively reduced. As used herein, "water-insoluble" refers to solubility in water at 25° C. of less than 0.04%.

DETAILED DESCRIPTION OF THE INVENTION

The bis-biguanide compounds of this invention have the generic formula:

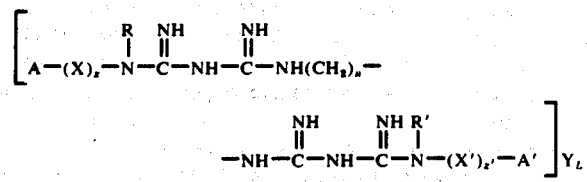

wherein A and A′ each represent either (1) a phenyl radical which optionally is substituted by an alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X′ each represent an alkylene radical containing from 1 to 3 carbon atoms; wherein $z$ and $z'$ each can be either 0 or 1; wherein R and R′ each represent either hydrogen, an alkyl radical containing from 1 to about 12 carbon atoms, or an aralkyl radical containing from 7 to about 12 carbon atoms; wherein $n$ is an integer from 2 to 12 inclusive; wherein the polymethylene chain $(CH_2)_n$ may optionally be interrupted by up to 5 oxygen or sulfur atoms, aromatic nuclei, etc.; and wherein each Y is an anion forming a relatively water-insoluble salt with the bis-biguanide cation and L is a number from about 1 to 4. Specific examples of these bis-biguanide compounds are disclosed hereinafter.

The above compounds are effective anti-plaque agents which demonstrate anti-caries and anti-gingivitis activity. Furthermore, when compositions containing these compounds are used continuously in a program of oral hygiene, only a limited amount of stain forms on the oral surfaces as compared with water-soluble bis-biguanide salts. This stain problem prevents compositions containing the water-soluble bis-biguanide compounds from being accepted by the consumer. The bis-biguanide compounds are normally used in amounts of from about 0.01 to about 2.5% by weight of the composition, preferably from about 0.05% to about 1.2%, and most preferably from about 0.1% to about 0.8%. Depending upon the composition, lesser or greater amounts may be used. In general, all that is required is to have an effective amount of the bis-biguanide salt in the mouth sufficient to give anti-plaque and/or anti-caries effectiveness.

Preferred anions, Y, are those disclosed in the abandoned U.S. Patent application of John William Haefele having Ser. No. 267,816, filed June 30, 1972, and the U.S. patent application of John William Haefele having Ser. No. 463,495, filed April 24, 1974, now U.S. Pat. No. 3,934,002, issued Jan. 20, 1976, both of said applications being incorporated herein by reference. Also, as disclosed in said applications, excess phosphorus anticalculus agent can be used to give additional stain reduction.

These anions are derived from the phosphorous anticalculus agents selected from the group consisting of those of the formulae:

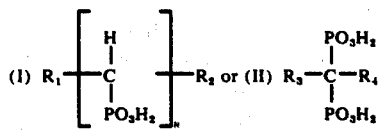

wherein $R_1$ and $R_2$ are hydrogen or $CH_2OH$; $n$ is an integer of from 3 to 10; $R_3$ is hydrogen, alkyl containing from 1 to about 20 carbon atoms, alkenyl containing from 2 to about 20 carbon atoms, aryl (e.g., phenyl and naphthyl), phenylethenyl, benzyl, halogen (e.g., chlorine, bromine, and fluorine), amino, substituted amino (e.g., dimethylamino, diethylamino, N-hydroxy-N-ethylamine, acetylamino), $-CH_2COOH$, $-CH_2PO_3H_2$, $-CH(PO_3H_2)(OH)$ or $-CH_2CH(PO_3H_2)_2$; $R_4$ is hydrogen, lower alkyl (e.g., methyl, ethyl, propyl, and butyl), amino, benzyl, halogen (e.g., chlorine, bromine and fluorine), hydroxyl, —CH₂COOH, —CH₂PO₃H₂, or —CH₂CH₂PO₃H₂;

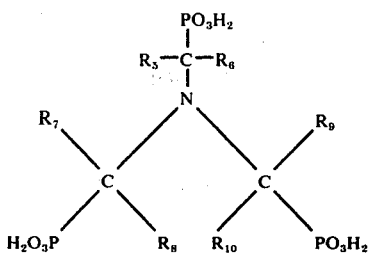

wherein R₅, R₆, R₇, R₈, R₉ and R₁₀ are each hydrogen or lower alkyl;

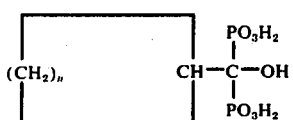

wherein n is an integer from 3 to 9;

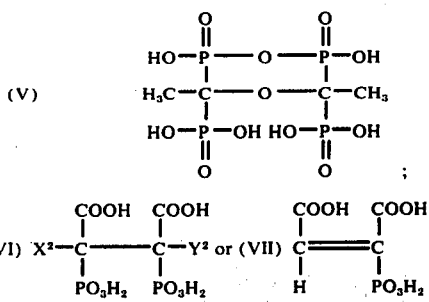

wherein X² and Y² are each hydrogen or hydroxy; or the condensation products of ammonia and phosphorus pentoxide, e.g.,

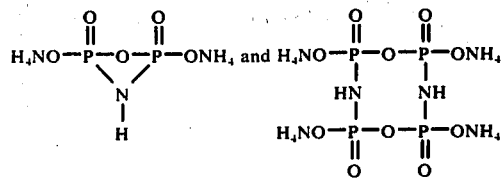

Operable polyphosphonates of the above fomula (I) include propane-1,2,3-triphosphonic acid; butane-1,2,3,4-tetraphosphonic acid; hexane-1,2,3,4,5,6-hexaphosphonic acid; hexane-1-hydroxy-2,3,4,5,6-pentaphosphonic acid; hexane-1,6-dihydroxy-2,3,4,5-tetraphosphonic acid; pentane-1,2,3,4,5-pentaphosphonic acid; heptane-1,2,3,4,5,6,7-heptaphosphonic acid; octane-1,2,3,4,5,6,7,8-octaphosphonic acid; nonane-1,2,3,4,5,6,7,8,9-nonaphosphonic acid; and decane-1,2,3,4,5,6,7,8,9,10-decaphosphonic acid.

Propane-1,2,3-triphosphonic acid and salts thereof can be prepared by a process disclosed in the commonly assigned application of D. Allan Nicholson and Darrel Campbell, Ser. No. 694,002, filed Dec. 27, 1967, now abandoned in favor of Divisional Application Ser. No. 82,819, filed Oct. 21, 1970, now U.S. Pat. No. 3,743,668, issued July 3, 1973, referred to in my parent application.

Butane-1,2,3,4-tetraphosphonic acid and salts thereof can be prepared by a process disclosed in the commonly assigned application of D. Allan Nicholson and Darrel Campbell, Ser. No. 694,003, filed Dec. 27, 1967, now abandoned in favor of Divisional Application Ser. No. 67,200, filed Aug. 8, 1970, now U.S. Pat. No. 3,755,504, issued Aug. 28, 1973, referred to in my parent application.

The higher aliphatic vicinal polyphosphonates and salts thereof can be prepared by the process disclosed in U.S. Pat. No. 3,584,035, D. Allan Nicholson and Darrel Campbell, issued June 8, 1971.

Among the operable polyphosphonates encompassed by the above formula (II) are ethane-1-hydroxy-1,1-diphosphonic acid; methanediphosphonic acid; methanehydroxydiphosphonic acid; ethane-1,1,2-triphosphonic acid, propane-1,1,3,3tetraphosphonic acid ethane-2-phenyl-1,1-diphosphonic acid; ethane-2-naphthyl-1,1-diphosphonic acid; methanephenyldiphosphonic acid; ethane-1-amino-1,1-diphosphonic acid; methanedichlorodiphosphonic acid; nonane-5,5-diphosphonic acid; n-pentane-1,1-diphosphonic acid; methanedifluorodiphosphonic acid; methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-ene-1-hydroxy-1,1-diphosphonic acid; octadec-9-ene-1-hydroxy-1,1-diphosphonic acid; 3-phenyl-1,1-diphosphonoprop-2-ene; octane-1,1-diphosphonic acid; dodecane-1,1-diphosphonic acid; phenylaminomethanediphosphonic acid; naphthylaminomethanediphosphonic acid; N,N-dimethylaminomethanediphosphonic acid; N-(2-hydroxyethyl)-aminomethanediphosphonic acid; N-acetylamino-methanediphosphonic acid; and aminomethanediphosphonic acid.

Operable examples of compounds having formula (III) include: the preferred tris(phosphonoalkyl)amines for the purpose of this invention — tris(phosphonomethyl) amine; tris(1-phosphonoethyl)amine; tris(2-phosphono-2-propyl)amine; and their pharmaceutically acceptable salts. Tris(phosphonomethyl)amine is especially preferred. The following additional compounds are exemplary of those which can be used herein:

a. bis(phosphonomethyl)-1-phosphonethyl amine;
b. bis(phosphonomethyl)-2-phosphono-2-propyl amine;
c. bis(1-phosphonethyl)phosphonomethyl amine;
d. bis(2-phosphono-2-propyl)phosphonomethyl amine;
e. tris(1-phosphono-1-pentyl)amine;
f. bis(phosphonomethyl)-2-phosphono-2-hexyl amine; and
g. the pharmaceutically acceptable salts of acids (a) through (f), e.g., the sodium, potassium, calcium, magnesium, ammonium, triethanolammonium, diethanolammonium, and monoethanolammmonium salts.

Mixtures of any of the foregoing tris(phosphonoalkyl)amines can be used in the compositions of this invention.

Examples of compounds coming within the formula (IV) include the following: Methanecyclobutylhydroxydiphosphonic acid; methanecyclopentylhydroxydiphosphonic acid; methanecyclohexylhydroxydiphosphonic acid; methanecycloheptylhydroxydiphosphonic acid; methanecyclooctylhydroxydiphosphonic acid, methanecyclononylhydroxydiphosphonic acid; methanecyclodecylhydroxydiphosphonic acid.

Especially preferred methanecycloalkylhydroxydiphosphonates for the purpose of this invention are methanecyclopentylhydroxydiphosphonic acid, methanecyclohexylhydroxydiphosphonic acid; and methanecycloheptylhydroxydiphosphonic acid.

Operable carboxyphosphonates of the above formula (VI) include ethane-1,2-dicarboxy-1,2-diphosophonic acid; ethane-1,2-dicarboxy-1,2-dihydroxy-1,2-diphosphonic acid; and ethane-1,2-dicarboxy-1-hydroxy-1,2-diphosphonic acid.

Among the operable carboxyphosphonates encompassed by the above formula (VII) are ethene-1,2-dicarboxy-1-phosphonic acid. While the above formula (VII) is representative of cis-isomers, the corresponding trans-isomers are also useful herein. Reference hereinafter to ethene-1,2-dicarboxy-1-phosphonic acid or salts thereof, unless otherwise specified, is intended as contemplating the cis- and trans-isomers and mixtures thereof.

Mixtures of any of the foregoing polyphosphonic acids and/or their pharmaceutically acceptable salts can be used in the practice of this invention. "Pharmaceutically acceptable salts" include the alkali metal, e.g., sodium, potassium and lithium; alkaline earth metal, e.g., magnesium, calcium, and strontium, ammonium; indium; stannous; and substituted ammonium, e.g., mono-, di-and triethanolammonium salts. It will be recognized that the soluble salts are required for reaction with a water-soluble bis-biguanide compound to form the insoluble bis-biguanide compound.

Ethane-1-hydroxy-1,1-diphosphonic acid, an especially preferred anticalculus agent, has the molecular formula $CH_3C(OH)(PO_3H_2)_2$. (According to nomenclature by radicals, the acid might also be named 1-hydroxyethylidene diphosphonic acid.) This compound can be prepared by any suitable method. However, an especially preferred method is disclosed in Quimby et al, U.S. Pat. No. 3,400,149, issued Sept. 3, 1968.

Other anions which form insoluble bis-biguanide salts include bisulfite, polymaleate, phosphite, hypophosphite, perfluorooctanoate, silicate, sorbate, salicylate, maleate, tartrate, citrate, fumarate, ethylenediaminetetraacetate, iminodiacetate, cinnamate, thiocyanate, arginate, pyromellitate, tetracarboxybutyrate, benzoate, glutarate, and perfluoropropionate anions. As can be seen, some of these anions are polyfunctional anions and since the bis-biguanides are polyfunctional cations, insoluble polymeric compounds will result. Preferred anions include citrate, tartrate, fumarate, and cinnamate anions.

The pH of the compositions of this invention is preferably maintained within the range of from about 4 to about 9. Below about 4, there can be some damage to dental enamel. Above about 9, the alkalinity becomes cosmetically undesirable and may irritate soft tissue in the mouth. The most preferred pH range is from about 6.0 to about 7.5.

In addition to the essential water-insoluble bis-biguanide compound of this invention as described in the foregoing, such compositions can also contain carriers suitable for use in the oral cavity. Such carriers include the usual components of toothpaste, toothpowder, mouthwash, prophylaxis pastes and the like as more fully described hereinafter.

A dentrifice, especially toothpaste, containing an anti-calculus agent is a preferred embodiment of this invention. Toothpaste compositions conventionally contain abrasive materials, sudsing agents, binders, humectants, flavoring and sweetening agents.

The abrasive should preferably be onw which does not adsorb the bis-biguanide compound.

Suitable sudsing agents are those which are reasonably stable and form suds throughout a wide pH range, and which will not react with the chlorhexidine, i.e., nonsoap nonionic, cationic, zwitterionic and amphoteric organic synthetic detergents.

The nonionic synthetic detergents which can be used with the oral compositions of the present invention may be broadly defined as compounds produced by the condensation of alkylene oxide groups (hydrophilic in nature) with an organic hydrophobic compound which may be aliphatic or alkyl-aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic". These compounds are formed by condensing ethylene oxide with a hydrophobic base formed by the condensation of propylene oxide with propylene glycol. The hydrophobic portion of the molecule which, of course, exhibits water insolubility has a molecular weight of from about 1,500 to about 1,800. The addition of polyoxyethylene radicals to this hydrophobic portion tends to increase the water solubility of the molecule as a whole and the liquid character of the products is retained up to the point where polyoxyethylene content is about 50% of the total weight of the condensation product.

Other suitable nonionic synthetic detergents include:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine — products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide group with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula, $R_1R_2R_3N \rightarrow O$, wherein $R_1$ contains an alkyl, alkenyl or monohydroxy alkyl radical of from about 8 to about 18 carbon atoms from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semi-polar bond. Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula $RR'R''P \rightarrow O$, wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are:
dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)-phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contains alkyl, alkenyl, hydroxy alkyl, or keto alkyl radicals containing from about 8 to about 20 carbons atoms, from 0 to about 10 ethylene oxide moieties and from 0 to 1 glyceryl moiety. Examples include:
octadecyl methyl sulfoxide, 2-ketotridecyl methyl sulfoxide,
3,6,9-trioxaoctadecyl 2-hydroxyethyl sulfoxide,
dodecyl methyl sulfoxide,
oleyl 3-hydroxy propyl sulfoxide,
tetradecyl methyl sulfoxide,
3-methoxytridecyl methyl sulfoxide
3-hydroxytridecyl methyl sulfoxide,
3-hydroxy-4-dodecoxybutyl methyl sulfoxide.

The zwitterionic synthetic detergents useful in the oral compositions of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water solubilizing group, e.g., carboxy., sulfonate, sulfate, phosphate, or phosphonate. A general formula for these compounds is:

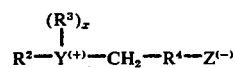

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorous, and sulfur atoms; $R^3$ is an alkyl or monohydroxyalkyl group containing 1 to about 3 carbon atoms; $x$ is 1 when Y is a sulfur atom and 2 when Y is a nitrogen or phosphorus atom, $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradecoxylphosphonio]-2-hydroxypropane-1-phosphate;
3-[N,N-dipropyl-N-3-dodecoxy-2hydroxypropylammonio]-propane-1-phosphonate;
3-(N,N-dimethyl-N-hexadecylammonio]propane-1-sulfonate;
3-N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]2-hydroxypentane-1-sulfate.

The cationic detergents useful in the oral compositions of the present invention can be broadly defined as quaternary ammonium compounds having 1 long alkyl chain containing from about 8 to about 18 carbon atoms such as lauryl trimethylammonium chloride; cetyl pyridinium chloride; cetyl trimethylammonium bromide; di-isobutylphenoxyethoxyethyldimethylbenzylammonium chloride; coconutalkyltrimethylammonium nitrite; cetyl pyridinium fluoride; etc. Especially preferred are the quaternary ammonium fluorides described in Briner et al, U.S. Pat. No. 3,535,421, issued October 20, 1970, incorporated by reference hereinbefore, where said quaternary ammonium fluorides have detergent properties.

The amphoteric synthetic detergents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate.

Examples of compounds falling within this definition are sodium 3-dodecylaminopropionate, sodium 3-dodecylaminopropane sulfonate, dodecyl-β-alanine, n-alkyltaurines such as the one prepared by reacting dodecylamine with sodium isethionate according to the teaching of Kosmin; U.S. Pat. No. 2,658,072, issued November 3, 1953, N-higher alkyl aspartic acids such as those produced according to the teaching of Lynch; U.S. Pat. No. 2,438,091, issued November 16, 1948, and the products sold under the trademark "Miranol" and described in Mannheimer; U.S. Pat. No. 2,528,378, issued Oct. 31, 1950.

The sudsing agent can be present in the dentifrice compositions of this invention in an amount from 0.5% to 5.0% by weight of the total compositions.

It is preferable to have a water-soluble fluoride compound present in an amount to give a fluoride concentration of from about 0.0025% to about 5.0%, preferably from about 0.005%, to provide additional anticaries effectiveness. Suitable fluoride sources are disclosed in the EXAMPLES. Preferred fluorides are sodium fluoride, indium fluoride, stannous fluoride, and sodium monofluorophosphate. The latter is especially preferred when the fluoride is present with the phosphorus-containing anticalculus agent to avoid damage to silicate fillings. Briner et al, U.S. Pat. No. 3,535,421, issued Oct. 20, 1970 and Agricola et al's abandoned U.S. Pat. Application Ser. No. 329,783, filed Feb. 9, 1973, are incorporated herein by reference.

All parts, percentages and ratios herein are by weight unless otherwise indicated.

In preparing toothpastes, it is necessary to add some thickening material to provide a desirable consistency. Preferred thickening agents are hydroxyethyl cellulose and water-soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerine, sorbitol, and other edible polyhydric alcohols. The humectant can comprise up to about 36% by weight of the toothpaste composition.

Suitable flavoring agents include oil of wintergreen, oil of peppermint, oil of spearmint, oil of sassafras, and oil of clove. Sweetening agents which can be used include saccharin, dextrose, levulose and sodium cyclamate.

Several representative oral compositions illustrating this invention are set forth in the following examples.

EXAMPLE I

A solution was prepared containing 0.2 gram chlorhexidine [1,6-di($N_1,N_1$'-p-chlorophenyldiguanido-$N_5,N_5$')-hexane] digluconate; 1.0 gram disodium ethane-1-hydroxy-1,1-diphosphonate ("EHDP"); 0.025 gram sodium hydroxide; and 98.78 grams water, said solution having a pH of about 6.5. A precipitate forms. The resulting slurry, when used in the mouth, inhibits the formation of plaque, calculus, and caries, but with continued use, does not form the large amount of stain that would result if the "EHDP" was not present. Gingivitis is also retarded.

EXAMPLE II

A solution was prepared containing 0.2 gram chlorhexidine digluconate; 1.0 gram of a nonionic surfactant, "Brij. 35 SP" [polyoxyethylene (23) lauryl ether]; 1.0 grams "EHDP"; 0.25 gram sodium hydroxide; and 97.78 grams water, said solution having a pH of about 6.5. The above solution inhibits the formation of plaque, calculus and caries as compared to water and when compared to 0.2% aqueous chlorhexidine solution at pH 6.5 gives less stain. Similar solutions in the pH range from about 5 to about 9 are also effective.

EXAMPLE III 0.025 gram sodium fluoride was added to 100 grams of the solution of Example II. This solution inhibits the formation of plaque and calculus, and in addition, has greater anti-caries effectiveness.

EXAMPLE IV

A solution was prepared containing 0.2 gram chlorhexidine digluconate; 1.0 gram "Victamide" (the condensation product of ammonia and phosphorus pentoxide); 1.0 gram polyoxyethylene (20) sorbitan monolaurate; 0.036 gram sodium hydroxide; and 97.76 grams water, the solution having a pH of 6.5. This solution, when used in the mouth on a regular basis, inhibits the formation of plaque, calculus and caries without excessive stain formation.

Several mouthwash compositions illustrating this invention are set forth in the following examples.

| Ingredient | Ex. | V | VI | VII | VIII | IX | X | XI | XII | XIII | XIV | XV |
|---|---|---|---|---|---|---|---|---|---|---|---|---|
| Glycerine | | 10.0 | 10.0 | 10.0 | 10.0 | 10.0 | 10.0 | 10.0 | 10.0 | 10.0 | 10.0 | 10.0 |
| Ethyl alcohol | | 16.5 | 16.5 | 16.5 | 16.5 | 16.5 | 16.5 | 16.5 | 16.5 | 16.5 | 16.5 | 16.5 |
| Polyoxyethylene (20) sorbitan monoisostearate | | 1.00 | 1.00 | 1.00 | 1.50 | 1.50 | 1.50 | 1.50 | 1.50 | 1.50 | 2.00 | 2.00 |
| Sodium saccharin | | .045 | .045 | .045 | .045 | .045 | .045 | .045 | .045 | .045 | .045 | .045 |
| Chlorhexidine digluconate | | 0.1 | 0.2 | 1.0 | 1.5 | 1.5 | 1.0 | 0.75 | 0.70 | 0.7 | 2.4 | 1.0 |
| Flavor | | .088 | .088 | .088 | .088 | .088 | .088 | .088 | .088 | .088 | .088 | .088 |
| $Mg_2$propane-1,1,3,3-tetraphosphonate | | 0.5 | | | | | | | | | | |
| $Na_2$propane-2,2-diphosphonate | | | 1.0 | | | | | | | | | |
| $(NH_4)_4$ethane-2-carboxy-1,1-diphosphonate | | | | 1.5 | | | | | | | | |
| Nonane-5,5-diphosphonic acid | | | | | | 1.75 | | | | | | |
| n-pentane-1,1-diphosphonic acid | | | | | | | 2.0 | | | | | |

-continued

| Ingredient | Ex. | V | VI | VII | VIII | IX | X | XI | XII | XIII | XIV | XV |
|---|---|---|---|---|---|---|---|---|---|---|---|---|
| Ethane-2-phenyl-1,1-diphosphonic acid | | | | | | 2.25 | | | | | | |
| Pent-4-ene-1-hydroxy-1,1-diphosphonic acid | | | | | | | 2.5 | | | | | |
| Octadec-9-ene-1-hydroxy-1,1-diphosphonic acid | | | | | | | | 3.0 | | | | |
| Methanedichlorodiphosphonic acid | | | | | | | | | 3.5 | | | |
| 3-phenyl-1,1-diphosphonoprop-2-ene | | | | | | | | | | 5.0 | | |
| Victamide (condensation product of ammonia and phosphorus pentoxide) | | | | | | | | | | | | 1.5 |
| Sodium fluoride | | | | | | | | | | | 0.10 | |
| Water | | | | | | | balance | | | | | |
| Adjust pH to 7. | | | | | | | | | | | | |

EXAMPLE XVI

A toothpowder which constitutes yet another embodiment of this invention has the following formulation:

| Component | Percent by Weight |
|---|---|
| Calcium pyrophosphate | 91.30 |
| Polyoxyethylene (20) sorbitan monolaurate | 1.30 |
| Sodium saccharin | 0.25 |
| Flavoring | 1.45 |
| Chlorhexidine diacetate | 0.70 |
| Trisodium ethane-1-hydroxy-1,1-diphosphonate | 5.00 |

When diluted with water and brushed upon the teeth in the conventional manner, this composition has a pH of approximately 7.0. The composition retards the formation of plaque, calculus, and caries without excessive staining.

The trisodium ethane-1-hydroxy-1,1-diphosphonate employed in the above formulation can be replaced by an equimolar amount of dipotassium ethane-1-amino-1,1-diphosphonate; dimagnesium ethane-2-carboxy-1,1-diphosphonate; phenylaminomethanediphosphonic acid; or N,N-dimethylaminomethanediphosphonic acid with substantially equivalent results.

EXAMPLE XVII

A propylaxis paste for use in the dental office for removal of stains and polishing the tooth surface after mechanical removal of calculus is formulated as follows:

| Component | Parts by Weight |
|---|---|
| Composition A: | |
| Navajo pumice | 77.1 |
| TiO$_2$ | 4.0 |
| Glycerine | 17.757 |
| Hydroxyethylcellulose | .222 |
| Sodium saccharin | .326 |
| Methanedibromodiphosphonic acid | 2.5 |
| Composition B: | |
| Chlorhexidine digluconate | 2.7 |
| Water | 87.00 |

Immediately prior to use 5.5 gm. of composition A are mixed with composition B to attain the desired texture and adjusted to pH 7.0. The paste is then applied to the tooth surfaces with a rubber propylactic cup in the conventional manner. This composition inhibits the formation of plaque, calculus, and caries without adverse effects of stain formation.

The methanedibromodiphonic acid and this example can be replaced by an equimolar amount of N-(2-hydroxyethyl)aminomethyanediphosphonic acid; bis(-triethanolammonium) N-acetylaminomethanediphosphonate; diacalcium aminomethanediphophonate; diethanolammonium methanehydroxydiphosphonate; or tris(monoethanolammonium) nonane-1,1-diphosphonate with comparable results.

EXAMPLE XVIII

When in any of the previous examples the following phosphorus-containing anti-calculus agents are substituted, either wholly or in part, for the specified phosphoruscontaining anti-calculus agents, substantially equivalent results are obtained in that the formulas provide antiplaque, anti-calculus, and anti-caries activity without excessive staining of the oral surfaces and the corresponding insoluble bis-biguanide compounds are formed: disodium salt of ethane 1,2-dicarboxy-1,2-diphosphonic acid; dipotassium salt of ethane-1,2-dicarboxy-1,2-dihydroxy-1,2-diphosphonic acid; the monocalcium salt of ethene-1,2-dicarboxy-1-phosphonic acid; the mono-magnesium salt of ethane-1,2-dicarboxy-1-hydroxy-1,1-disphosphonic acid; the di(-triethanolammonium) salt of ethane-1,2-dicarboxy-1,2-diphosphonic acid rather than the disodium salt of ethane-1,2-dicarboxy-1,2-diphosphonic acid; diammonium salt of ethane-1,2-diphosphonic acid; monocalcium salt of ethane-1,2-dicarboxy-1,2-dihydroxy-1,2-diphosphonic acid; distannous salt of ethane-1,2-dicarboxy-1-hydroxy-1,2-diphosphonic acid; indium salt of ethene-1,2-dicarboxy-1-phosphonic acid; traimmonium salt of ethane-1,2-dicarboxy-1,2-dihydroxy-1,2-diphosphonic acid; trisodium salt of ethene-1,2-dicarboxy-1-phosphonic acid; distannous salt of ethane-1,2dicarboxy-1,2-diphosphonic acid; hexasodium salt of cyclic tetraphosphonic acid; trisodium salt of methane cyclohexylhydroxydiphosphonic acid; diammonium salt of methanecyclobutylhydroxydiphosphonic acid; monocalcium salt of methanecyclopentylhydroxydiphosphonic acid; distannous salt of methanecycloheptylhydroxydiphosphonic acid; indium salt of methanecyclooctylhydroxydiphophonic acid; triammonium salt of methanecyclononylhydroxydiphosphonic acid; trisodium salt of methanecyclodecylhydroxdiphosphonic acid; distannous salt of methanecyclohexylhydroxydiphosphonic acid; methanecycloalkylhydroxydiphophonic acid; tris(1-phosphonoethyl)amine; tetrasodium salt of tris(2-phosphono-2-propyl)

amine; dipotassium salt of bis(phosphonomethyl)-1-phosphonoethyl amine; monocalcium salt of bis(phosphonomethyl)-2-phosphono-2-propyl amine; monomagnesium salt of bis(1-phosphonoethyl)phosphonomethyl amine; distannous salt of bis(2-phosphono-2-propyl)phosphonomethyl amine; Victamide and mixtures thereof, e.g., 1:1 and 1:1:1 ratios.

EXAMPLE XIX

Another toothpaste prepared in accordance with this invention has the following composition:

| Component | Percent by Weight |
|---|---|
| Precipitated urea/formaldehyde condensate (abrasive) | 31.00 |
| Sorbitol (70% aqueous solution) | 6.25 |
| Glycerine | 18.00 |
| Polyoxyethylene (20) sorbitan monoisostearate | 1.50 |
| Hydroxyethylcellulose | 1.15 |
| Magnesium aluminum silicates | 0.40 |
| Sodium saccharin | 0.04 |
| Flavoring | 0.95 |
| Methanediphosphonic acid | 1.50 |
| Sodium monofluorophosphate | 3.00 |
| Sodium fluoride | 0.01 |
| Chlorhexidine digluconate | 1.50 |
| Water | balance |
| Mole ratio polyphosphonate/fluoride 2.4 | |
| pH adjusted to 7.5 with 5N NaOH | |

This composition is effective in retarding the formation of dental calculus when used in a conventional manner. This composition also inhibits plaque and caries without excessive staining.

EXAMPLE XX AND XXI

| Component | Percent by Weight Example XX | Example XXI |
|---|---|---|
| Chlorhexidine digluconate | 0.2 | 0.2 |
| "EHDP" | 1.0 | |
| Victamide | | 1.0 |
| Brij. 35 SP | 1.0 | 1.0 |
| Ethanol | 12.0 | 12.0 |
| Glycerol | 6.0 | 6.0 |
| Water | balance | balance |

EXAMPLE XXII

Dissolve 2 grams of NaHSO$_3$ in 50 ml. water; dissolve 0.2 gram chlorhexidine [1,6-di(N$_1$,N$_1$'-p-chlorophenyldiguanido-N$_5$,N$_5$')hexane] digluconate in 50 ml. water; mix the solutions, and adjust the suspension to pH 6.5 with a small amount of NaOH. The suspension inhibits the deposition of plaque on a surface in a plaque-development system comprising human saliva containing 2% sucrose added extra.

EXAMPLE XXIII

Dissolve 1 gram disodium etidronate (ethane-1-hydroxy-1,1-diphosphonate) in 50 ml. water; dissolve 0.2 gram chlorhexidine digluconate in 50 ml. water; mix. The pH is about 7. The slurry inhibits plaque in an in vitro system.

EXAMPLE XXIV

Dissolve 1 gram disodium etidronate and 0.25 gram NaF in 50 ml. water; dissolve 0.2 gram chlorhexidine digluconate in 50 ml. H$_2$O; mix. The pH is about 7, and the slurry inhibits plaque in an in vitro system.

EXAMLPLE XXV

A 1% aqueous solution of Brij. 35 SP is prepared. To 50 ml. of this is added 1 gram disodium etidronate; to another 50 ml. is added 0.2 gram chlorhexidine digluconate; the solutions are mixed, and a clear mixture results, pH about 7. The surfactant solubilizes the insoluble chlorhexidine salt in the micelles. The solution inhibits plaque in an in vitro test.

EXAMPLE XXVI

A 2% aqueous solution of sodium N-coconut sarcosinate and a 0.4% aqueous solution of chlorhexidine digluconate are mixed a equal volumes. The clear mixture, pH about 7, inhibits plaque in an in vitro test.

EXAMPLE XXVII

In 50 ml. of a 1% aqueous Brij. 35 SP solution is dissolved 2 grams sodium salicylate; in 50 ml. of a 1% aqueous Brij. 35 SP solution is dissolved 0.2 gram chlorhexidine digluconate; the solutions are mixed, and the pH of the clear mixture is adjusted to 6.5. The solution decreases stain formation on a tooth in an in vitro test as compared to chlorhexidine alone. In place of 2 grams sodium salicylate one can substitute, with substantially the same results, any one of the following: 2 grams sodium citrate; 2 grams sodium maleate; 2 grams sodium fumarate; 2 grams sodium tartrate; 2 grams sodium cinnamate; 2 grams sodium sorbate; 2 grams sodium polymaleate; 2 grams sodium pyromellitate; 2 grams sodium benzoate; 2 grams tetrasodium tetracarboxybutane; 2 grams sodium glutarate; 2 grams NaH$_2$PO$_3$ (phosphite); 2 grams NaH$_2$PO$_2$ (hypophosphite); 1 gram disodium ethylenediamine tetraacetate; 1 gram disodium iminodiacetate; 1 gram sodium perfluoropropionate; 5 grams sodium perfluorooctanoate; and 2 grams sodium phosphate.

EXAMPLE XXVIII

In 50 ml. of a 1% aqueous Brij. 35 SP solution is dissolved 0.6 gram arginine base; in 50 ml. of a 1 % aqueous Brij. 35 SP solution is dissolved 0.2 gram chlorhexidine digluconate; the solutions are mixed, and the clear mixture is adjusted to pH 7. It reduces the stain formation on a tooth in an in vitro test, compared to chlorhexidine digluconate alone.

EXAMPLE XXIX

In 50 ml. of a 1% aqueous Brij. 35 SP solution is dissolved 0.25 gram disodium etidronate and 0.05 gram sodium monofluorophosphate; in 50 ml. of a 1% aqueous Brij. 35 SP solution is dissolved 0.2 gram chlorhexidine digluconate. The solutions are mixed. The clear mixture inhibits in vitro stain.

When in the above examples the following watersoluble fluoride agents are substituted, either wholly or in part, for the sodium fluoride, substantially equivalent results are obtained in that the formulas provide additional anticaries activity: sodium monofluorophosphate, stannous fluoride, potassium fluoride, lithium fluoride, cesium fluoride, ammonium fluoride, aluminum fluoride, cupric fluoride, indium fluoride, stannous fluorozirconate, lead fluoride, ferric fluoride, nickel fluoride, palladium fluoride, silver fluoride, zinc fluoride, zirconium fluoride, hexylamine hydrofluoride, laurylamine hydrofluoride, myristylamine hydrofluoride, decanolamine hydrofluoride, octadecenylacmine hydrofluoride, myristoxyamine hydrofluoride, diethylaminoethyloctoylamide hydrofluoride, diethanolaminoethyloleylamide hydrofluoride, diethanolaminopropyl-N'-octadecenylamine dihydrofluoride, 1-ethanol-2-hexadecylimidazoline dihydrofluoride, octoylethanolamine hyrofluoride, octyltrimethylammonium fluoride, dodecylethyldimethylammonium fluoride, tetraethylammonium fluoride, dilauryldimethylammonium fluoride, $\Delta^{8,9}$-octadecenylbenzyldimethylammonium fluoride, dioctyldiethylammonium fluoride, cyclohexylcetyldimethylammonium fluoride, furfuryllauryldimethylammonium fluoride, phenoxyethylcetyldimethylammonium fluoride, N:N'-tetramethyl-N:N'-dilaurylethylene-diammonium difluoride, N-cetylpyridinium fluoride, N:N-dilauryl-morpholinium fluoride, N-myristyl-N-ethylmorpholinium fluoride, N-(octylaminocarbonylethyl)-N-benzyl-dimethylammonium fluoride, N-($\beta$-hydroxydodecyl)trimethylammonium fluoride, N-phenyl-N-hexadecyldiethylammonium fluoride, N-cyclohexyl-N-octadecyldimethylammonium fluoride, N-(2-carbomethoxyethyl)-N-benzyl-dimethylammonium fluoride, N-(2-carbocyclohexoxyethyl-N-myristyldimethylammonium fluoride, N-(2-carbobenzyloxyethyl)-N-dodecyldimethylammonium fluoride, N-[2-(N:N'-dimethylamino-carbonyl)-ethyl]-N-dodecyldiethylammonium fluoride, N-carboxymethyl-N-eicosyldimethylammonium fluoride, betaine hydrofluoride, sarcosine stannous fluoride, alanine stannous fluoride, glycine potassium fluoride, sarcosine potassium fluoride, glycine hyrofluoride, lysine hydrofluoride, alanine hydrofluoride, betaine zirconium fluoride, and mixtures thereof in, e.g., 1:1 proportions.

When in the above examples the following surfaceactive agents are inserted in an amount of from about 1 to 2% as an additional ingredient, substantially equivalent results are obtained, except that the compositions have enhanced detergency effects: polypropylene glycol (M.W. 1700) polyoxyethylene (M.W. 1500); polyoxypropylene (70) ethylenediamine polyoxyethylene (100); coconut alcohol polyoxyethylene (20); dimethyldodecylamine oxide; oleyldi(2-hydroxyethyl)amine oxide; dimethyloctylamine oxide; dimethyldecylamine oxide; dimethyltetradecylamine oxide; 3,6,9-trioxaheptadecyldiethylamine oxide; di(2-hydroxyethyl)-tetradecylamine oxide; 2-dodecoxyethyldimethylamine oxide; 3-dodecoxy-2-hydroxypropyldi(3-hydroxypropyl)amine oxide; dimethylhexadecylamine oxide; dodecyldimethylphosphine oxide; tetradecyldimethylphosphine oxide; tetradecylmethylethylphosphine oxide; 3,6,9-trioxaoctadecyldimethylphosphine oxide; cetyldimethylphosphine oxide; 3-dodecoxy-2-hydroxypropyldi(2-hydroxyethyl)phosphine oxide; stearyldimethylphosphine oxide; cetylethylpropylphosine oxide; oleyldiethylphosphine oxide; dodecyldiethylphosphine oxide; tetradecyldiethylphosphine oxide; dodecyldipropylphosphine oxide; dodecyldi(hydroxymethyl)phosphine oxide; dodecyldi(2-hydroxyethyl)phosphine oxide; tetradecylmethyl-2-hydroxypropylphosphine oxide; oleyldimethylphosphine oxide; 2-hydroxydodecyldimethylphosphine oxide; octadecyl methyl sulfoxide; 2-ketotridecyl methyl sulfoxide; 3,6,9-trioxaoctadecyl 2-hydroxyethyl sulfoxide; dodecyl methyl sulfoxide; oleyl 3-hydroxypropyl sulfoxide; tetradecyl methyl sulfoxide; 3-methoxytridecyl methyl sulfoxide; 3-hydroxytridecyl methyl sulfoxide; 3-hydroxy-4-dodecoxybutyl methyl sulfoxide; 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetradecoxylphosphonio]-2-hydroxypropane-1-phosphate; 3-[N,N-dipropyl-N-3-dodecoxy-2-hydroxypropylammonio]-propane-1-phosphonate; 3-(N,N-dimethyl-N-hexadecylammonio)propane-1-sulfonate; 3-N,N-dimethyl-N-hexadecylamonio)-2-hydroxypropane-1-sulfonate; 4-[N,N-di(2-hydroxyethyl)-N-(2-hydroxydodecyl) ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; 5-[N,N-di(3-hydroxypropyl)-N-hexadecylammonio]2-hydroxypentane-1-sulfate; dodecyltrimethylammonium chloride; nonylbenzylethyldimethylammonium nitrate; tetradecylpyridinium bromide; octadecyl-butylpropylmethylphosphonium nitrite; decyldimethylsulfonium chloride; (hexylphenyl)dimethylbenzylammonium fluoride; eicosyldimethylbenzylphosphonium chloride; coconutalkylmethylmorpholinium nitrate; octadecylmethylbenzylsulfonium sulfate; laurylpyridinium chloride; laurylpyridinium bromide; laurylpryidinium bisulfate; laurylpyridinium-5-chloro-2-mercaptobenzothiazole; laurylpicolinium-p-toluene-sulfonate; tetradecylpyridinium bromide; cetylpyridinium chloride; cetylpyridinium bromide; laurylisoquinolinium bromide; laurylisoquinolinium saccharinate; alkylisoquinolinium bromide; N-cetyl-N-ethyl-morpholinium ethosulfate; benzalkonium chloride; monoquaternaries $R_4N^+X^-$ (one R group is fatty); octadecyltrimethylammonium chloride; coconut alkyl trimethylammonium chloride; dodecylbenzyltri(octyldecyl)ammonium chloride; monoquaternaries $R_4N^+X^-$ (two R groups are fatty); dihexadecyldimethylammonium chloride; di-coconut alkyl dimethylammonium chloride; monoquaternaries $R_4N^+X^-$ (three R groups are fatty); tri(hydrogenated tallow) methylammonium chloride; distilled tallow amine acetate; diamine acetates; N-oleyl propylene diamine monoacetate; condensation product of octyl phenol with 15 moles of ethylene oxide per mole of octyl phenol; dimethyldodecylamine oxide; dodecyldimethylphosphine oxide; tetradecyl methyl sulfoxide; 3-(N,N-dimethyl-N-hexadecylammonio)propane-1-sulfonate; 3-dodecylaminopropionate; and dodecyl-$\beta$-alanine.

When in the above examples, the following bis-biguanide compounds are substituted, either wholly or in part (50%) for the preferred chlorhexidine digluconate, substantially equivalent results are obtained in that plaque, calculus, gingivitis and caries are inhibited with reduced staining as compared to the use of the bisbiguanide compounds alone: 1,6-bis-(2-ethylhexylbiguanidohexane)dihydrochloride; 1,6-di-($N_1$, $N_1'$-phenyldiguanido-$N_5$, $N_5'$)-hexane tetrahydrochloride; 1,6-di($N_1$, $N_1'$-phenyl-$N_1$, $N_1'$-methyldiguanido-$N_5$, $N_5'$)-hexane dihydrochloride; 1,6-di($N_1,N_1'$-o-chlorophenyldiguanido-$N_5$, $N_5'$)-hexane dihydrochloride; 1,6-di($N_1$, $N_1'$-2,6-dichlorophenyldiguanido-$N_5,N_5'$)hexane dihydrochloride; 1,6-di[$N_1$, $N_1'$-$\beta$-(p-methoxyphenyl)diguanido-$N_5,N_5'$]-hexane dihydrochloride; 1,6-di($N_1,N_1'$-$\alpha$-methyl-$\beta$-phenyldiguanido-$N_5,N_5'$)-hexane dihydrochlorie; 1,6-di($N_1$, $N_1'$-p-nitrophenyldiguanido-$N_5,N_5'$)-hexane dihydrochloride; $\omega$:$\omega'$-di($N_1$, $N_1'$-phenyldiguanido-$N_5,N_5'$)-di-n-propylether dihydrochloride; $\omega$:$\omega'$-di($N_1$, $N_1'$-p-chlorophenyldiguanido-$N_5,N_5'$)-di-n-propylether tetrahydrochloride; 1,6-di($N_1,N_1'$-2,4-dichlorophenyldiguanido-$N_5,N_5'$)hexane tetrahydrochloride; 1,6-di($N_1$, $N_1'$-p-methylphenyldiguanido-$N_5,N_5'$)-hexane dihydrochloride; 1,6-di($N_1,N_1'$-2,4,5-trichlorophenyldiguanido- $N_5,N_5'$)hexane tetrahydrochloride; 1,6-di[$N_1,N_1'$-α-(p-chlorophenyl)ethyldiguanido-$N_5,N_5'$]hexane dihydrochloride; ω:ω'-di($N_1,N_1'$-p-chlorophenyldiguanido-$N_5,N_5'$)m-xylene dihydrochloride; 1,12-di-($N_1,N_1'$-p-chlorophenyldiguanido-$N_5,N_5'$)dodecane dihydrochloride; 1,10-di($N_1,N_1'$-phenyldiguanido-$N_5,N_5'$)decane tetrahydrochloride; 1,12-di($N_1,N_1'$-phenyldiguanido-$N_5,N_5'$)dodecane tetrahydrochloride; 1,6-d8($N_1,N_1'$-o-chlorophenyldiguanido-$N_5,N_5'$)hexane dihydrochloride; 1,6-di($N_1,N_1'$-p-chlorophenyldiguanido-$N_5,N_5'$)-hexane tetrahydrochloride; ethylene bis(1-tolyl biguanide); ethylene bis(p-tolyl biguanide); ethylene bis(3,5-dimethylphenyl biguanide); ethylene bis(p-tert-amylphenyl biguanide); ethylene bis(nonylphenyl biguanide); ethylene bis(phenyl biguanide); ethylene bis(N-butylphenyl biguanide); ethylene bis(2,5-diethoxyphenyl biguanide); ethylene bis(2,4-dimethylphenyl biguanide); ethylene bis(o-diphenyl biguanide); ethylene bis(mixed amyl naphthyl biguanide); N-butyl ethylene bis(phenyl biguanide); trimethylene bis(o-tolyl biguanide); N-butyl trimethylene bis(-phenylbiguanide); tetramethylene bis(1-tolyl biguanide); the specific compounds disclosed in U.S. Pat. No. 2,863,919, Birtwell et. al., (Dec. 9, 1958), said patent being incorporated herein by reference; the specific compounds disclosed in U.S. Pat. No. 3,468,898, Cutler et. al., (September 23, 1969), said patent being incorporated herein by reference; and the corrrresponding pharmaceutically acceptable salts of all of the above such as the acetates; gluconates; and hydrochlorides.

What is claimed is:

1. An oral composition effective in inhibiting the formation of plaque, caries and calculus, said composition comprising a carrier suitable for use in the oral cavity and from about 0.01% to about 2.5% by weight of a water-soluble bis-biguanide compound having the generic formula:

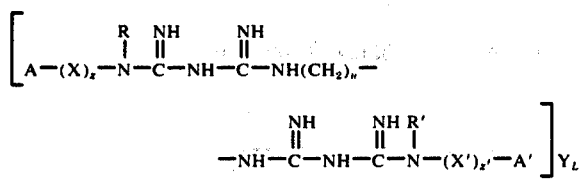

wherein A and A' each are selected from the group consisting of
A. substituted and unsubstituted phenyl radicals wherein the substituents are selected from the group consisting of up to two groups selected from the group consisting of alkyl and alkoxy groups containing from 1 to about 4 carbon atoms, a nitro group, and a halogen atom;
B. an alkyl group containing from 1 to about 12 carbon atoms; and
C. alicyclic groups containing from 4 to about 12 carbon atoms;

wherein X and X' each represent an alkylene radical containing from 1 to 3 carbon atoms; wherein $z$ and $z'$ each are selected from the group consisting of 0 and 1; wherein R and R' each are selected from the group consisting of hydrogen, an alkyl radical containing from 1 to about 12 carbon atoms, and aralkyl radical containing from 7 to about 12 carbon atoms; wherein $n$ is an integer from 2 to 12 inclusive; wherein the polymethylene chain $(CH_2)_n$ can be interrupted by up to 5 moieties selected from the group consisting of ether, thioether, phenyl, and naphthyl; wherein L is a number from about 1 to 4; and wherein Y is an anion which will form a pharmaceutically acceptable water-insoluble bis-biguanide compound, said anion being derived from a compound selected from the group consisting of bisulfites, polymaleates, phosphites, hypophosphites, perfluorooctanoates, silicates, sorbates, salicylates, maleates, tartrates, citrates, fumarates, ethylenediamine tetraacetates, iminodiacetates, cinnamates, thiocyanates, arginates, pyromellitates, tetracarboxybutyrates, benzoates, glutarates, perfluoropropionates and polyphosphonates selected from the group consisting of:

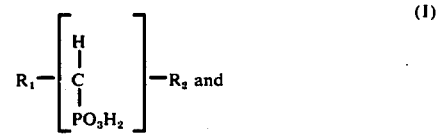

wherein in both formulae $R_1$ and $R_2$ are selected from the group consisting of hydrogen and $CH_2OH$; $n$ is an integer of from 3 to 12; $R_3$ is selected from the group consisting of hydrogen, alkyl containing from 1 to about 20 carbon atoms, alkenyl containing from 2 to about 20 carbon atoms, phenyl, naphthyl, phenylethenyl, benzyl, halogen, amino, dimethylamino, diethylamino, N-hydroxy-N-ethylamino, acetylamino, $-CH_2COOH$, $-CH_2PO_3H_2$, $-CH(PO_3H_2)(OH)$ and $-CH_2CH(PO_3H_2)_2$; and $R_4$ is selected from the group consisting of hydrogen, lower alkyl, amino, benzyl, halogen, hydroxyl, $-CH_2COOH$, $-CH_2PO_3H_2$, and $-CH_2CH_2PO_3H_2$;

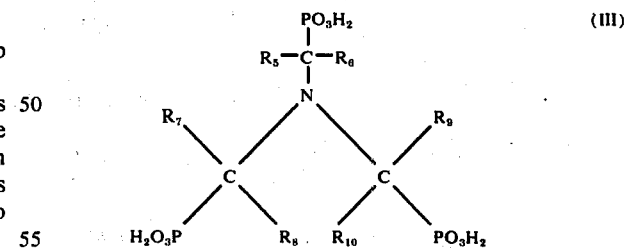

wherein $R_5$, $R_6$, $R_7$, $R_8$, $R_9$, and $R_{10}$ are each selected from the group consisting of hydrogen and lower alkyl;

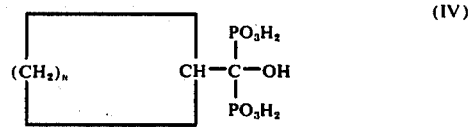

wherein $n$ is an integer from 3 to 9;

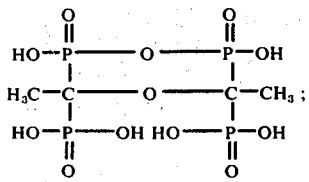
(V)

carboxyphosphonates selected from the group consisting of

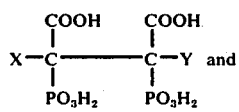
(VI)

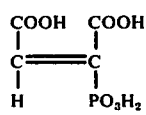
(VII)

wherein X and Y are each selected from the group consisting of hydrogen and hydroxy; and the condensation products of ammonia and phosphorous pentoxide, said condensation products consisting of the compounds

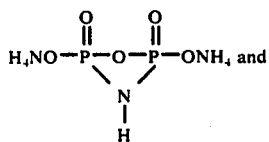
(VIII)

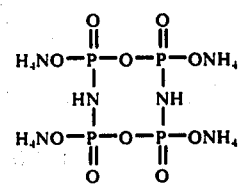
(IX)

2. A composition in accordance with claim 1 which has a pH within the range of from about 4 to about 9.

3. A composition in accordance with claim 2 which contains from about 0.05% to about 1.2% by weight of the bis-biguanide compound and which has a pH of from about 6 to about 7.5.

4. A composition in accordance with claim 3 wherein $A — (X)_z$ and $A' — (X')_{z'}$, each represent and ethylhexyl group and $n$ is 6.

5. A composition in accordance with claim 3 wherein A and A' are each p-chlorophenyl groups, z and z' are 0, and $n$ is 6.

6. A composition in accordance with claim 3 which contains a water-soluble source of fluoride in a quantity sufficient to provide fluoride in an amount of from about 0.025% to about 5.0% as $F^-$.

7. A composition in accordance with claim 1 wherein the compound from which the anion Y is derived is a polyphosphate selected from the group consisting of:

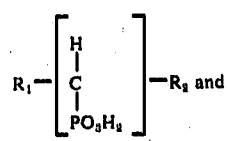
(I)

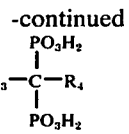
(II)

wherein in both formulae $R_1$ and $R_2$ are selected from the group consisting of hydrogen and $CH_2OH$; $n$ is an integer of from 3 to 12; $R_3$ is selected from the group consisting of hydrogen, alkyl containing from 1 to about 20 carbon atoms, alkenyl containing from 2 to about 20 carbon atoms, phenyl, naphthyl, phenylethenyl, benzyl, halogen, amino, dimethylamino, diethylamino, N-hydroxy-N-ethylamino, acetylamino, $—CH_2COOH$, $—CH_2PO_3H_2$, $—CH(PO_3H_2)(OH)$ and $—CH_2CH(PO_3H_2)_2$; and $R_4$ is selected from the group consisting of hydrogen, lower alkyl, amino, benzyl, halogen, hydroxyl, $—CH_2COOH$, $—CH_2PO_3H_2$, and $—CH_2CH_2PO_3H_2$;

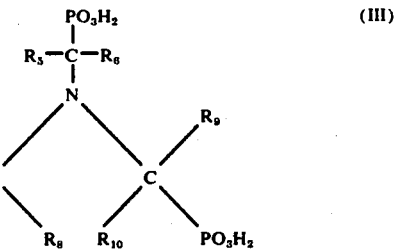
(III)

wherein $R_5$, $R_6$, $R_7$, $R_8$, $R_9$, and $R_{10}$ are each selected from the group consisting of hydrogen and lower alkyl;

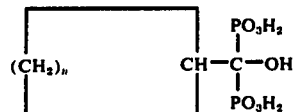
(IV)

wherein $n$ is an integer from 3 to 9;

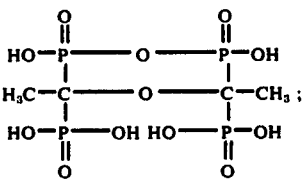
(V)

carboxyphosphonates selected from the group consisting of

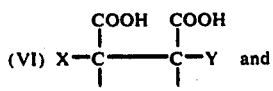
(VI)

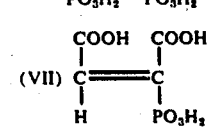
(VII)

wherein X and Y are each selected from the group consisting of hydrogen and hydroxy; and the condensation products of ammonia and phosphorous pentoxide, said condensation products consisting of the compounds

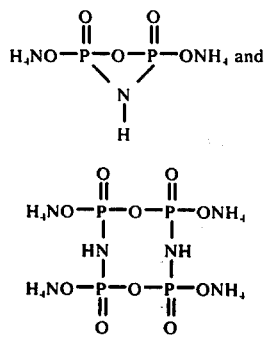

8. A composition in accordance with claim 7 which has a pH within the range of from about 4 to about 9.

9. A composition in accordance with claim 8 which contains from about 0.05% to about 1.2% by weight of the bis-biguanide compounds, and which has pH of from about 6 to about 7.5.

10. A composition in accordance with claim 9 wherein $A — (X)_z$ and $A'— (X')_z'$, each represent an ethylhexyl group and $n$ is 6.

11. A composition in accordance with claim 9 wherein A and A' are each p-chlorophenyl groups, z and z' are 0, and $n$ is 6.

12. A composition in accordance with claim 11 wherein the bis-biguanide compound is [1,6-di($N_1$, $N_1'$-p-chlorophenyldiguanido-$N_5$, $N_5'$)-hexane] ethane-1-hydroxy-1,1-diphosphonate.

13. A composition in accordance with claim 12 which contains a water-soluble source of fluoride in a quantity sufficient to provide fluoride in an amount of from about 0.025% to about 5.0% as $F^-$.

14. A composition in accordance with claim 1 wherein the compound from which the anion Y is derived is selected from the group consisting of bisulfites, polymaleates, phosphites, hypophosphites, perfluorooctanoates, silicates, sorbates, salicylates, maleates, tartrates, citrates, fumarates, ethylenediamine tetraacetates, iminodiacetates, cinnamates, thiocyanates, arginates, pyromelitates, tetracarboxybutyrates, benzoates, glutarates, and perfluoropropionates.

15. A composition in accordance with claim 14 which has a pH within the range of from about 4 to about 9.

16. A composition in accordance with claim 15 which contains from about 0.05% to about 1.2% by weight of the bis-biguanide compound, and which has a pH of from about 6 to about 7.5.

17. A composition in accordance with claim 16 wherein $A — (X)_z$ and $A'— (X')_z'$, each represent an ethylhexyl group and $n$ is 6.

18. A composition in accordance with claim 17 wherein the compound from which the anion Y is derived is selected from the group consisting of citrates, tartrates, fumarates, and cinnamates.

19. A composition in accordance with claim 16 wherein A and A' are each p-chlorophenyl groups, z and z' are 0, and $n$ is 6.

20. A composition in accordance with claim 19 wherein the compound from which the anion Y is derived is selected from the group consisting of citrates, tartrates, fumarates and cinnamates.

21. A composition in accordance with claim 16 which contains a water-soluble source of fluoride in a quantity sufficient to provide fluoride in an amount of from about 0.025% to about 5.0% as $F^-$.

* * * * *